US008247344B2

(12) United States Patent
Shin et al.

(10) Patent No.: US 8,247,344 B2
(45) Date of Patent: Aug. 21, 2012

(54) MULTI-METAL OXIDE CATALYST AND METHOD FOR PRODUCING (METH)ACRYLIC ACID BY USING THE SAME

(75) Inventors: Hyun-Jong Shin, Metropolitan (KR); Byung-Yul Choi, Naju-si (KR); Yeon-Shick Yoo, Naju-si (KR); Young-Jin Cho, Naju-si (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 13/081,632

(22) Filed: Apr. 7, 2011

(65) Prior Publication Data

US 2011/0245535 A1 Oct. 6, 2011

Related U.S. Application Data

(62) Division of application No. 12/309,648, filed as application No. PCT/KR2007/003489 on Jul. 19, 2007, now Pat. No. 7,943,710.

(30) Foreign Application Priority Data

Jul. 27, 2006 (KR) .............................. 2006-0071061

(51) Int. Cl.
*C07C 51/25* (2006.01)
*C07C 51/16* (2006.01)
*B01J 23/24* (2006.01)

(52) U.S. Cl. ......... 502/312; 562/547; 562/546; 562/535

(58) Field of Classification Search .................. 502/312; 562/547, 546, 535
See application file for complete search history.

(56) References Cited

U.S. PATENT DOCUMENTS

| 6,383,978 B1 | 5/2002 | Bogan, Jr. |
| 2004/0192966 A1* | 9/2004 | Hazin et al. .................. 562/547 |
| 2005/0065372 A1 | 3/2005 | Borgmeier et al. |

FOREIGN PATENT DOCUMENTS

| JP | 05-293389 | 11/1993 |
| JP | 09-176102 | 7/1997 |
| WO | WO 2005/063674 A1 | 7/2005 |

* cited by examiner

*Primary Examiner* — William Cheung
(74) *Attorney, Agent, or Firm* — McKenna Long & Aldridge LLP

(57) ABSTRACT

The present invention provides a Mo—Bi—Nb based composite metal oxide (with the proviso that Te is not included); a method for producing (meth)acrylic acid from at least one reactant selected from the group consisting of propylene, propane, isobutylene, t-butyl alcohol and methyl-t-butyl ether, in which a Mo—Bi—Nb based composite metal oxide (with the proviso that Te is not included) is used as a catalyst; and a reactor used for producing (meth)acrylic acid from at least one reactant selected from the group consisting of propylene, propane, isobutylene, t-butyl alcohol and methyl-t-butyl ether, in which a Mo—Bi—Nb based composite metal oxide (with the proviso that Te is not included) is used as a catalyst. Further, the present invention provides a method for producing the (meth)acrylic acid without any additional process of converting (meth)acrolein into (meth)acrylic acid.

8 Claims, 1 Drawing Sheet

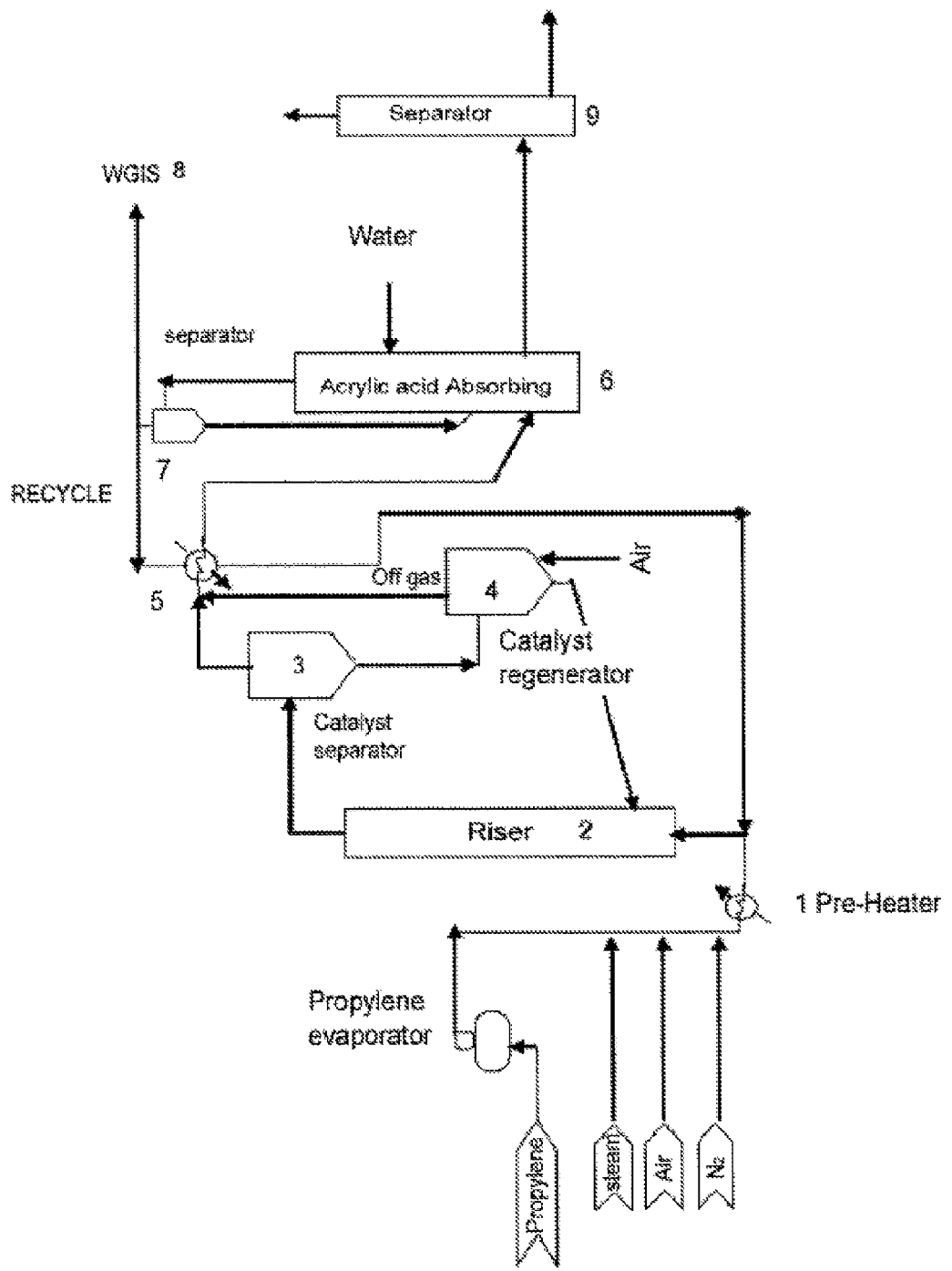

MULTI-METAL OXIDE CATALYST AND METHOD FOR PRODUCING (METH)ACRYLIC ACID BY USING THE SAME

This application is a divisional application of U.S. patent application Ser. No. 12/309,648, filed on Jan. 26, 2009, which is a national stage application of International Application No. PCT/KR2007/003489, filed on Jul. 19, 2007, now U.S. Pat. No. 7,943,710, which claims priority from Korea Patent Application No. 10-2006-71061 filed on Jul. 27, 2006 in the KIPO, the entire contents of which are fully incorporated herein by reference.

TECHNICAL FIELD

The present invention relates to a Mo—Bi—Nb based composite metal oxide (multi-metal oxide), and a method for producing (meth)acrylic acid from propylene or the like by using the Mo—Bi—Nb based composite metal oxide as a catalyst. Further, the present invention relates to a method for producing (meth)acrylic acid from propylene or the like by an one-step catalyst reaction.

BACKGROUND ART

A process for producing an unsaturated fatty acid from olefin by way of an unsaturated aldehyde is a typical process of gas-phase catalytic oxidation.

Particular examples thereof include a process of producing (meth)acrylic acid from a staring material such as propylene, propane, isobutylene, t-butyl alcohol or methyl-t-butyl ether (referred to as 'propylene or the like', hereinafter) by way of corresponding (meth)acrolein.

In this connection, in the first step of partially oxidizing olefins to unsaturated aldehyde, composite metal oxides containing molybdenum and bismuth are generally used as a catalyst. In the second step of partially oxidizing the unsaturated aldehyde, which is a main product of the first step, to unsaturated fatty acid, composite metal oxides containing molybdenum and vanadium are used as a catalyst.

More particularly, in the first step, propylene or the like is oxidized by oxygen, inert gas for dilution, water steam and a certain amount of a catalyst, so as to produce (meth)acrolein as a main product. Then, in the second step, the (meth)acrolein is oxidized by oxygen, inert gas for dilution, water steam and a certain amount of a catalyst, so as to produce (meth)acrylic acid. The catalyst used in the first step is a Mo—Bi based multinary metal oxide, which oxidizes propylene or the like to produce (meth)acrolein as a main product. Also, some (meth)acrolein is continuously oxidized on the same catalyst to partially produce (meth)acrylic acid. The catalyst used in the second step is a Mo—V based multinary metal oxide, which mainly oxidizes (meth)acrolein of the mixed gas containing the (meth)acrolein produced from the first step to produce (meth)acrylic acid as a main product.

A reactor for performing the aforementioned process is provided either in such a manner that both the two-steps can be performed in one system, or in such a manner that the two steps can be performed in different systems.

As mentioned above, the first-step catalyst involved in gas-phase partial oxidation using propylene or the like as a starting material is the Mo—Bi based multinary metal oxide, with which (meth)acrolein is produced as a main product and 10% or less of (meth)acrylic acid is produced.

As disclosed in JP-A-8-3093, a conventional first-step catalyst is a composite oxide represented by the formula of $Mo_a$—$Bi_b$—$Fe_c$-$A_d$-$B_e$—$C_f$-$D_g$-$O_x$ (wherein Mo, Bi and Fe represent molybdenum, bismuth and iron, respectively; A is nickel and/or cobalt; B is at least one element selected from the group consisting of manganese, zinc, calcium, magnesium, tin and lead; C is at least one element selected from the group consisting of phosphorus, boron, arsenic, Group 6B elements in the Periodic Table, tungsten, antimony and silicon; D is at least one element selected from the group consisting of potassium, rubidium, cesium and thallium; when a=12, 0<b≦10, 0<c≦10, 1≦d≦10, 0≦e≦10, 0≦f≦20, and 0<g≦2; and x is a value defined by the oxidation state of each element). When gas-phase catalytic oxidation of propylene is performed with molecular oxygen by using the first-step catalyst, and by operating the first-step catalyst bed at a temperature of 325° C., acrolein is produced with a yield of 81.3% and acrylic acid is produced with a yield of 11%. In other words, acrylic acid content is low in the reaction product obtained by using the first-step catalyst.

Meanwhile, JP-A-5-293389 discloses a catalyst represented by the formula of $Mo_aBi_bFe_cA_dX_eY_fZ_gSi_hO_i$ (wherein Mo, Bi, Fe, Si, and O represent molybdenum, bismuth, iron, silicon and oxygen, respectively; A is at least one element selected from the group consisting of cobalt and nickel; X is at least one element selected from the group consisting of magnesium, zinc, manganese, calcium, chrome, niobium, silver, barium, tin, tantalum and lead; Y is at least one element selected from the group consisting of phosphorus, boron, sulfur, selenium, Group 6B elements in the Periodic Table, cerium, tungsten, antimony and titanium; Z is at least one element selected from the group consisting of lithium, sodium, potassium, rubidium, cesium and thallium; and each of a, b, c, d, e, f, g, h and i represents the atomic ratio of each element, with the proviso that when a=12, b=0.01 to 3, c=0.01 to 5, d=1 to 12, e=0 to 6, f=0 to 5, g=0.001 to 1, and h=0 to 20, and i is the oxygen atom number needed to satisfy the atomic valence of each element). When gas-phase catalytic oxidation of propylene is performed by using the above catalyst to produce acrolein and acrylic acid, acrylic acid is produced with a yield of 6.2 mole % under a propylene conversion ratio of 99.1 mole % and an acrolein selectivity of 89.6 mole %. In other words, acrylic acid content is still low in the reaction product obtained by using the first-step catalyst.

Further, the known production process comprising the two-steps of partial oxidation requires a separate reactor or reaction zone in each reaction step, and catalysts having different compositions are provided according to the requirements of each step. That is, hardware (physical operating system) should be controlled and supervised under the optimal reaction conditions, of which complexity gives troubles and difficulties in operation.

DISCLOSURE

Technical Problem

The present invention provides a catalyst capable of producing (meth)acrylic acid with high productivity, in which the above mentioned problems are solved by using a simple and economical method, that is, one-step catalyst reaction.

Further, the present invention provides an one-step reaction process for stably producing (meth)acrylic acid at high yield over a long period of time, in which problems such as a hotspot problematic in a typical exothermic reaction, degradation and a reduction in yield due to the hotspot can be solved by packing of a desirable catalyst.

Technical Solution

The present invention provides a Mo—Bi—Nb based composite metal oxide (with the proviso that Te is not included).

Further, the present invention provides a process for producing (meth)acrylic acid using at least one reactant selected from the group consisting of propylene, propane, isobutylene, t-butyl alcohol and methyl-t-butyl ether by using a Mo—Bi—Nb based composite metal oxide (with the proviso that Te is not included) as a catalyst.

Furthermore, the present invention provides a process for producing (meth)acrylic acid using at least one reactant selected from the group consisting of propylene, propane, isobutylene, t-butyl alcohol and methyl-t-butyl ether by using a Mo—Bi—Nb based composite metal oxide as a catalyst, without any additional process of converting (meth)acrolein into (meth)acrylic acid.

Further, the present invention provides a reactor for producing (meth)acrylic acid using at least one reactant selected from the group consisting of propylene, propane, isobutylene, t-butyl alcohol and methyl-t-butyl ether, in which a Mo—Bi—Nb based composite metal oxide is used as a catalyst.

Advantageous Effects

According to the present invention, when the first-step catalyst comprising a Mo—Bi—Nb based composite metal oxide as an essential component is only used in the production of (meth)acrylic acid using propylene or the like, yield and/or selectivity of (meth)acrylic acid increases in the reaction products, and thus the second oxidation step and a separate catalyst required for conversion of (meth)acrolein to acrylic acid in the conventional two-step process are not needed, and the heat of formation is effectively controlled by packing of an efficient catalyst. As a result, (meth)acrylic acid can be stably produced with high yield for a long period of time.

DESCRIPTION OF DRAWINGS

FIG. 1 is a schematic view illustrating the structure of fluidized bed reactor capable of using a catalyst according to the present invention.

BEST MODE

Mo—Bi based first-step metal oxide catalysts for producing (meth)acrolein by oxidation of propylene or the like, which have been disclosed to date, generally provide selectivity from propylene or the like to (meth)acrolein and (meth)acrylic acid of about 90 mole % or more, wherein the molar ratio of (meth)acrolein to (meth)acrylic acid in the first-step reaction product is about 9:1. Additionally, when the first-step reaction product is subjected to the second-step reaction, it is possible to obtain a product comprising (meth)acrylic acid as a main product from (meth)acrolein.

The present inventors have found that when a Mo—Bi based first-step metal oxide catalyst also containing Nb, that is, a Mo—Bi—Nb based composite metal oxide is prepared and used as the first-step reaction catalyst, (meth)acrylic acid is produced using propylene at yield of 60 mole % or more by catalytic reaction during an one-step process.

Therefore, as compared to other Mo—Bi based metal oxides used as the first-step reaction catalyst in the conventional two-step reaction process, when the Mo—Bi—Nb based composite metal oxide according to the present invention is used as a catalyst, provided is higher selectivity of (meth)acrylic acid in the reaction products obtained by the catalytic reaction using the catalyst. As a result, the additional second step of catalytic reaction, in which (meth)acrolein is converted into (meth)acrylic acid, can be minimized or excluded. Accordingly, in the present invention, (meth)acrylic acid can be produced from propylene or the like at high yield, by one-step process comprising a single series of catalyst or by a reaction comprising a minimized two-step catalyst reaction, which is impossible with the conventional catalyst composition.

(1) The Mo—Bi—Nb based composite metal oxide of the present invention is preferably a composite metal oxide represented by the following Formula 1.

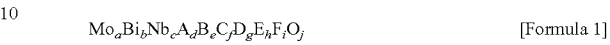

$$Mo_aBi_bNb_cA_dB_eC_fD_gE_hF_iO_j$$ [Formula 1]

wherein Mo represents molybdenum, Bi represents bismuth, and Nb represents niobium;

A is at least one element selected from the group consisting of W, Sb, As, P, Sn and Pb;

B is at least one element selected from the group consisting of Fe, Zn, Cr, Mn, Cu, Pd, Ag and Ru;

C is at least one element selected from the group consisting of Co, Cd, Ta, Pt and Ni;

D is at least one element selected from the group consisting of Si, Al, Zr, V and Ce;

E is at least one element selected from the group consisting of Se, Ga, Ti, Ge, Rh and Au;

F is at least one element selected from the group consisting of Na, K, Li, Rb, Cs, Ca, Mg, Sr, Ba and MgO;

each of a, b, c, d, e, f, g, h, i, and j represents the atomic ratio of each element; and when a=12, b is 0.01 to 20, c is 0.001 to 20, d is 0 to 15, e is 0 to 20, f is 0 to 20, g is 0 to 10, h is 0 to 10, i is 0 to 10, and j is a value defined by the oxidation state of each of the above elements.

When used as a catalyst, the Mo—Bi—Nb based composite metal oxide according to the present invention may be used alone or may be supported on an inert carrier. Examples of the carrier include porous or non-porous alumina, silica-alumina, silicon carbide, titanium dioxide, magnesium oxide, aluminum sponge, or the like. Additionally, the carrier may take a cylindrical shape, a hollow cylindrical shape, or a spherical shape, but is not limited thereto. For example, a catalyst having a cylindrical shape preferably has a ratio of length to diameter (outer diameter) (L/D ratio) of 1 to 1.3, and more preferably has an L/D ratio of 1. A catalyst having a cylindrical or spherical shape preferably has an outer diameter of 3 to 10 mm, more preferably of 4 to 8 mm.

The Mo—Bi—Nb based composite metal oxide according to the present invention may be prepared by a typical method for producing a composite metal oxide, except that a different composition is used.

There is no particular limitation in the shape of a metal precursor forming the Mo—Bi—Nb based composite metal oxide. For example, a compound that is provided originally in the form of an oxide or can be converted into an oxide by heating (i.e. calcination) at least in the presence of oxygen, for example, halogenide, nitride, formate, oxalate, citrate, acetate, carbonate, amine complex, ammonium salt and/or hydroxide may be used as a starting material.

According to an embodiment of the present invention, the method for preparing the composite metal oxide comprises the steps of: dissolving or dispersing a predetermined amount (stoichiometric amount) of each starting material containing each element in an aqueous medium; heating the resultant solution or dispersion under stirring; allowing the system to evaporate to obtain a dry solid and drying and pulverizing the solid; and molding the powder into a desired shape via extrusion molding to obtain tablets or granules. In this case, glass fibers and inorganic fibers including various kinds of whiskers, which are known to improve the strength and frictional resistance, may be further added. Additionally, in order to control the properties of the catalyst for excellent reproducibility, other additives known as powder binders, such as ammonium nitrate, cellulose, starch, polyvinyl alcohol, stearic acid, or the like, may be used.

The composite metal oxide catalyst according to the present invention may be obtained by calcining the molded product or the product supported on a carrier under a flow of 0.2 to 2 m/s at 200 to 600° C. for about 1 to 10 hours or more. The calcination step may be performed under an inert gas atmosphere, an oxidative atmosphere, for example, air (a mixture of inert gas and oxygen), or a reductive atmosphere (e.g., a mixture of inert gas, oxygen and $NH_3$, CO and/or $H_2$). The calcination step may be performed over a period of several minutes to several hours, and the calcination period generally decreases as the temperature increases.

(2) The Mo—Bi—Nb based composite metal oxide according to the present invention may be used as a catalyst to produce (meth)acrylic acid from at least one reactant selected from the group consisting of propylene, propane, isobutylene, t-butyl alcohol, and methyl-t-butyl ether.

In this case, among the reaction products obtained by catalytic action of the Mo—Bi—Nb based composite metal oxide, (meth)acrylic acid is produced at yield of 60 mole % or more.

Therefore, the Mo—Bi—Nb based composite metal oxide according to the present invention can be used as a catalyst producing (meth)acrylic acid from at least one reactant selected from the group consisting of propylene, propane, isobutylene, t-butyl alcohol and methyl-t-butyl ether, without any additional process of converting (meth)acrolein into (meth)acrylic acid.

Particularly, the Mo—Bi—Nb based composite metal oxide according to the present invention may be used as a catalyst for the first-step partial oxidation in a process for producing (meth)acrylic acid, the process comprising a first step for producing (meth)acrolein from the reactants such as propylene or the like and a second step for producing (meth)acrylic acid from the (meth)acrolein.

Moreover, the Mo—Bi—Nb based composite metal oxide according to the present invention may be used as a catalytic effective component of at least one catalyst bed, when the reaction zone in which (meth)acrylic acid is produced using at least one reactant selected from the group consisting of propylene, propane, isobutylene, t-butyl alcohol and methyl-t-butyl ether is packed with two or more catalyst beds.

When gas-phase catalytic oxidation is carried out by using the Mo—Bi—Nb based composite metal oxide according to the present invention as a catalyst, there is no particular limitation in systems and operation conditions thereof used in the process. Reactors that may be used in the present invention include conventional fixed-bed, fluidized-bed, and moving-bed reactors.

When the Mo—Bi—Nb based composite metal oxide according to the present invention is used as a catalyst for partial oxidation of propylene or the like, (meth)acrylic acid can be produced by an one-step process, whereby (meth) acrylic acid can be produced using a fluidized bed reactor as illustrated in FIG. 1.

In this connection, catalyst particles and reactants flow into the fluidized bed reactor, and after reaction, they flow out of the reactor. Then, they are cooled and circulated through the reactor.

With reference to FIG. 1, the fluidized bed reactor will be described in detail.

A reaction gas containing propylene or the like is preheated to reaction temperature in a heat exchanger 1, and the solid catalysts and reaction gas are mixed to pass through the fluidized bed reactor 2. The partial oxidation is generated in the reactor. Subsequently, non-reactants and products (e.g. acrylic acid) flow out of the reactor in a mixed state, and the solid catalysts and the produced gas are separated in a catalyst separator 3. The catalysts separated in the catalyst separator 3 regenerate the inactivated catalysts in a catalyst regenerator 4, and fresh catalysts are supplied. Meanwhile, the produced gas separated in the catalyst separator 3 is cooled to a temperature range for purification in a plate-type heat exchanger 5, and then supplied in a purification process. At this time, the plate-type heat exchanger 5 can be used for preheating a recycle gas.

In the fluidized bed reactor, since the particle size of catalyst is small and fluidized, the amount of heat generated on the surface of the catalyst particle can be minimized. Therefore, when (meth)acrylic acid is produced from propylene or the like in one-step process, instead of two-step process, the heat is not generated through two-step process, but simultaneously generated in one-step process, thereby causing a problematic hotspot. Thus, in order to solve the problem due to the hotspot, the fluidized bed reactor is more preferable than fixed bed reactor.

Meanwhile, example of the fixed-bed reactor includes a sell and tube type reactor, and the Mo—Bi—Nb based composite metal oxide of the present invention is packed into a reaction tube, and used as a fixed catalyst bed for producing (meth)acrylic acid. For example, the reaction zone for producing (meth)acrylic acid from a reactant such as propylene or the like can be packed with two or more of catalyst beds, and at this time, at least one of catalyst bed, in which a catalytic effective component is Mo—Bi—Nb based composite metal oxide, can be used.

Reaction conditions, which are generally adopted for producing (meth)acrylic acid and (meth)acrolein from a reactant such as propylene or the like via gas-phase catalytic oxidation, may be used. For example, a gas mixture as a starting material, which contains 4 vol % or more of reactants such as propylene or the like, 10 to 20 vol % of molecular oxygen, and 60 to 80 vol % of inert gas functioning as a diluent (e.g. nitrogen, carbon dioxide, steam, or the like), is caused to be in contact with the catalyst according to the present invention, at a temperature of 250 to 50° C. 0 under a pressure of 0.1 to 3 $kg/cm^2$ G with a space velocity of 300 to 5000 hr-1 (STP) to carry out a desired reaction.

(3) According to the present invention, (meth)acrylic acid can be stably produced with high yield for a long period of time, in which problems such as a hotspot problematic in a typical exothermic reaction, heat accumulation and a reduction in yield due to the hotspot can be solved by controlling the activity of a catalyst containing Mo—Bi—Nb based composite metal oxide and heat of catalytic reaction.

The catalytic activity can be controlled by the control of Nb/Mo ratio, catalyst calcination time, the amount of air supplied, and the catalyst size.

According to the present invention, (meth)acrylic acid can be produced by using the activity-controlled catalysts, in which the catalyst beds in each tube in the shell and tube reactor are packed with various types of catalysts in order to gradually increase their activity from inlet to outlet.

That is, the reaction zone can be packed with two or more of different catalyst beds so that the particle size of the catalyst in the catalyst beds having a catalytic effective component of Mo—Bi—Nb based composite metal oxide gradually decreases from the inlet, in which the reactants are introduced, to the outlet, in which the reaction products are outputted.

Mode for Invention

Hereinafter, the present invention will be described in detail with reference to Examples and Comparative Examples. However, these Examples are for illustrative purposes only, and the invention is not intended to be limited thereto.

Catalyst Preparation Example

Preparation Example 1

Catalyst 1

2500 ml of distilled water was heated and stirred at 70 to 85° C. and 1000 g of ammonium molybdate was dissolved therein to form a solution 1. Then, 274 g of bismuth nitrate, 228 g of ferrous nitrate and 2.3 g of potassium nitrate were added to 400 ml of distilled water, the materials were mixed thoroughly, 71 g of nitric acid was added thereto, and the materials were dissolved sufficiently to form a solution 2. 686 g of cobalt nitrate was dissolved in 200 ml of distilled water, so as to form a solution 3. After mixing the solution 2 with the solution 3, the mixed solution was further mixed with the solution 1 while the temperature was maintained at 40 to 60° C., so as to provide a catalyst suspension.

The catalyst suspension was dried and the obtained cake-shaped solid was pulverized into a size of 150 μm or less. The resultant catalyst powder was mixed with a predetermined amount of water for 2 hours, and formed into a cylindrical shape. The catalyst was formed to have a diameter of 5.0 mm and a height of 5.0 mm, and calcined at 500° C. for 5 hours under the air, resulting in a catalyst 1. The produced catalyst had the elemental composition of except oxygen. The resulting catalyst had the following elemental composition except oxygen:

$$Mo_{12}Bi_{1.2}Fe_{1.2}Co_5K_{0.05}$$

Preparation Example 2

Catalyst 2

Catalyst 2 was provided in the same manner as described in Preparation Example 1, except that 64 g of niobium chloride were further added to form a solution 1. The resulting catalyst had the following elemental composition except oxygen:

$$Mo_{12}Nb_{0.5}Bi_{1.2}Fe_{1.2}Co_5K_{0.05}$$

Preparation Example 3

Catalyst 3

Catalyst 3 was provided in the same manner as described in Preparation Example 1, except that 64 g of niobium chloride were further added to form a solution 1 and the molded catalyst was allowed to have a diameter of 7 mm and a height of 7 mm. The resulting catalyst had the following elemental composition except oxygen:

$$Mo_{12}Nb_{0.5}Bi_{1.2}Fe_{1.2}Co_5K_{0.05}$$

Preparation Example 4

Catalyst 4

Catalyst 4 was provided in the same manner as described in Preparation Example 1, except that 32 g of niobium chloride were further added to form a solution 1. The resulting catalyst had the following elemental composition except oxygen:

$$Mo_{12}Nb_{0.25}Bi_{1.2}Fe_{1.2}Co_5K_{0.05}$$

Preparation Example 5

Catalyst 5

Catalyst 5 was provided in the same manner as described in Preparation Example 1, except that 32 g of niobium chloride were further added to form a solution 1 and the molded catalyst was allowed to have a diameter of 7 mm and a height of 7 mm. The resulting catalyst had the following elemental composition except oxygen:

$$Mo_{12}Nb_{0.25}Bi_{1.2}Fe_{1.2}Co_5K_{0.05}$$

Example

Catalyst Packing and Catalytic Activity Test

To a 3 m stainless steel reactor having an inner diameter of 1 inch and heated with molten nitrate salt, alumina silica was packed to a height of 150 mm as an inert material, and any one or a mixture of Catalysts 1 to 5 prepared in Catalyst Preparation Examples 1 to 5 shown in Table 1 was packed to have a height of 2800 mm, from the inlet of the reaction gas toward the outlet.

The oxidation was performed by introducing feed gas containing 7 vol % of propylene, 13 vol % of oxygen, 12 vol % of water steam, and 68 vol % of inert gas onto the catalyst with a space velocity of 1500 hr-1 (STP), at a reaction temperature of 320° C. under a reaction pressure of 0.7 atm.

In Tables 1, conversion ratio of a reactant and yield are calculated, based on the following Mathematical Formulae 1 and 2.

Conversion ratio of propylene (%)=[(mole number of reacted propylene)/(mole number of supplied propylene)]×100   [Mathematical Formula 1]

Yield (%) of acrylic acid=[(mole number of produced acrylic acid)/(mole number of supplied propylene)]×100   [Mathematical Formula 2]

The experimental results of the Examples and Comparative Example are shown in the following Table 1.

TABLE 1

| Section | Catalyst packed | Conversion ratio of propylene (%) 320° C. | Yield (mole %) of acrylic acid |
|---|---|---|---|
| Compative 1 | Catalyst 1 (2800 mm) | 98.67 | 9.51 |
| Example 1 | Catalyst 2 (2800 mm) | 92.21 | 67.40 |
| Example 2 | Catalyst 3 (800 mm) + Catalyst 2 (2000 mm) | 91.44 | 72.65 |
| Example 3 | Catalyst 5 (800 mm) + Catalyst 4 (2000 mm) | 93.87 | 76.84 |

The invention claimed is:
1. A method for producing (meth)acrylic acid using at least one reactant selected from the group consisting of propylene, propane, isobutylene, t-butyl alcohol and methyl-t-butyl ether, wherein a Mo—Bi—Nb based composite metal oxide (with the proviso that Te is not included) represented by the following Formula 1 is used as a catalyst:

$Mo_aBi_bNb_cA_dB_eC_fD_gE_hF_iO_j$  [Formula 1]

wherein Mo represents molybdenum, Bi represents bismuth, and Nb represents niobium;

A is at least one element selected from the group consisting of W, Sb, As, P, Sn and Pb;

B is at least one element selected from the group consisting of Fe, Zn, Cr, Mn, Cu, Pd, Ag and Ru;

C is at least one element selected from the group consisting of Co, Cd, Ta, Pt and Ni;

D is at least one element selected from the group consisting of Si, Al, Zr, V and Ce;

E is at least one element selected from the group consisting of Se, Ga, Ti, Ge, Rh and Au;

F is at least one element selected from the group consisting of Na, K, Li, Rb, Cs, Ca, Mg, Sr, Ba and MgO;

each of a, b, c, d, e, f, g, h, i, and j represents the atomic ratio of each element; and wherein $a=12$, $0.01 \leq b \leq 20$, $0.001 \leq c \leq 20$, $0 \leq d \leq 15$, $0 < e \leq 20$, $0 < f \leq 20$, $0 \leq g \leq 10$, $0 \leq h \leq 10$, $0 < i \leq 10$, and j is a value defined by the oxidation state of each of the above elements.

2. The method according to claim 1, wherein a yield of (meth)acrylic acid of products obtained by catalytic action of the Mo—Bi—Nb based composite metal oxide is 60 mole % or more.

3. The method according to claim 1, wherein the method is performed in a fluidized bed reactor.

4. The method according to claim 1, further comprising a process of converting (meth)acrolein of the products produced by the catalytic action of the Mo—Bi—Nb based composite metal oxide into (meth)acrylic acid.

5. The method according to claim 1, wherein a reaction zone in which (meth)acrylic acid is produced using at least one reactant selected from the group consisting of propylene, propane, isobutylene, t-butyl alcohol and methyl-t-butyl ether is packed with two or more catalyst beds, and the Mo—Bi—Nb based composite metal oxide is used as a catalytic effective component of at least one catalyst bed.

6. The method according to claim 5, wherein the reaction zone is packed with two or more of catalyst beds having different catalytic activities in order to increase the catalytic activity of the catalyst bed from the inlet, in which the reactants are introduced, to the outlet, in which the reaction products are outputted.

7. The method according to claim 5, wherein the reaction zone is packed with two or more different catalyst beds so that the particle size of the catalyst in the catalyst beds having an effective component of Mo—Bi—Nb based composite metal oxide decreases from the inlet, in which the reactants are introduced, to the outlet, in which the reaction products are outputted.

8. The method according to claim 7, wherein the reaction zone is packed with two or more different catalyst beds having an effective component of mo-bi-nb based composite metal oxide and the different molar ratios of Nb to Mo ([Nb]/[Mo]) and the catalytic activity of each of the catalyst beds increases from the inlet, in which the reactants are introduced, to the outlet, in which the reaction products are outputted.

* * * * *